United States Patent [19]

Tarcy

[11] 4,428,800

[45] Jan. 31, 1984

[54] MEASUREMENT OF GASEOUS FLUORIDE CONCENTRATION USING AN INTERNAL REFERENCE SOLUTION

[75] Inventor: Gary P. Tarcy, Pittsburgh, Pa.

[73] Assignee: Aluminum Company of America, Pittsburgh, Pa.

[21] Appl. No.: 418,286

[22] Filed: Sep. 15, 1982

[51] Int. Cl.³ ............................................. G01N 27/46
[52] U.S. Cl. .................................. 204/1 T; 436/124; 436/125; 436/150; 422/98; 422/68
[58] Field of Search ................ 204/1 B; 436/124, 125, 436/150; 422/98, 68

[56] References Cited

U.S. PATENT DOCUMENTS

| | | | |
|---|---|---|---|
| 3,431,182 | 3/1969 | Frant | 204/1 B |
| 3,563,874 | 2/1971 | Ross et al. | 204/1 B |
| 3,960,523 | 6/1976 | Ryan | 55/84 |

OTHER PUBLICATIONS

Converse; J. G. et al., "Ion–Selective Electrode Analyzer for Monitoring Gaseous Hydrogen Chloride", ISA Transactions, vol. 15, No. 3, 1976, pp. 220–226.

Prior Art Public Use by Aluminum Company of America is discussed on p. 2 of patent specification.

*Primary Examiner*—Winston A. Douglas
*Assistant Examiner*—B. J. Boggs, Jr.
*Attorney, Agent, or Firm*—Glenn E. Klepac

[57] ABSTRACT

A method for measuring fluoride concentrations in a gas wherein a sample of the gas is mixed with an internal reference solution in a gas scrubber to form a fluoride-containing solution. The fluoride-containing solution is collected, and the concentration of fluoride ion is determined in a potentiometric apparatus. The apparatus includes a first electrode having a fluoride-sensitive element and a second electrode having an element sensitive to a halide ion other than fluoride ion. The improved method of the invention compensates for errors caused by evaporation of water from the gas scrubber.

11 Claims, 1 Drawing Figure

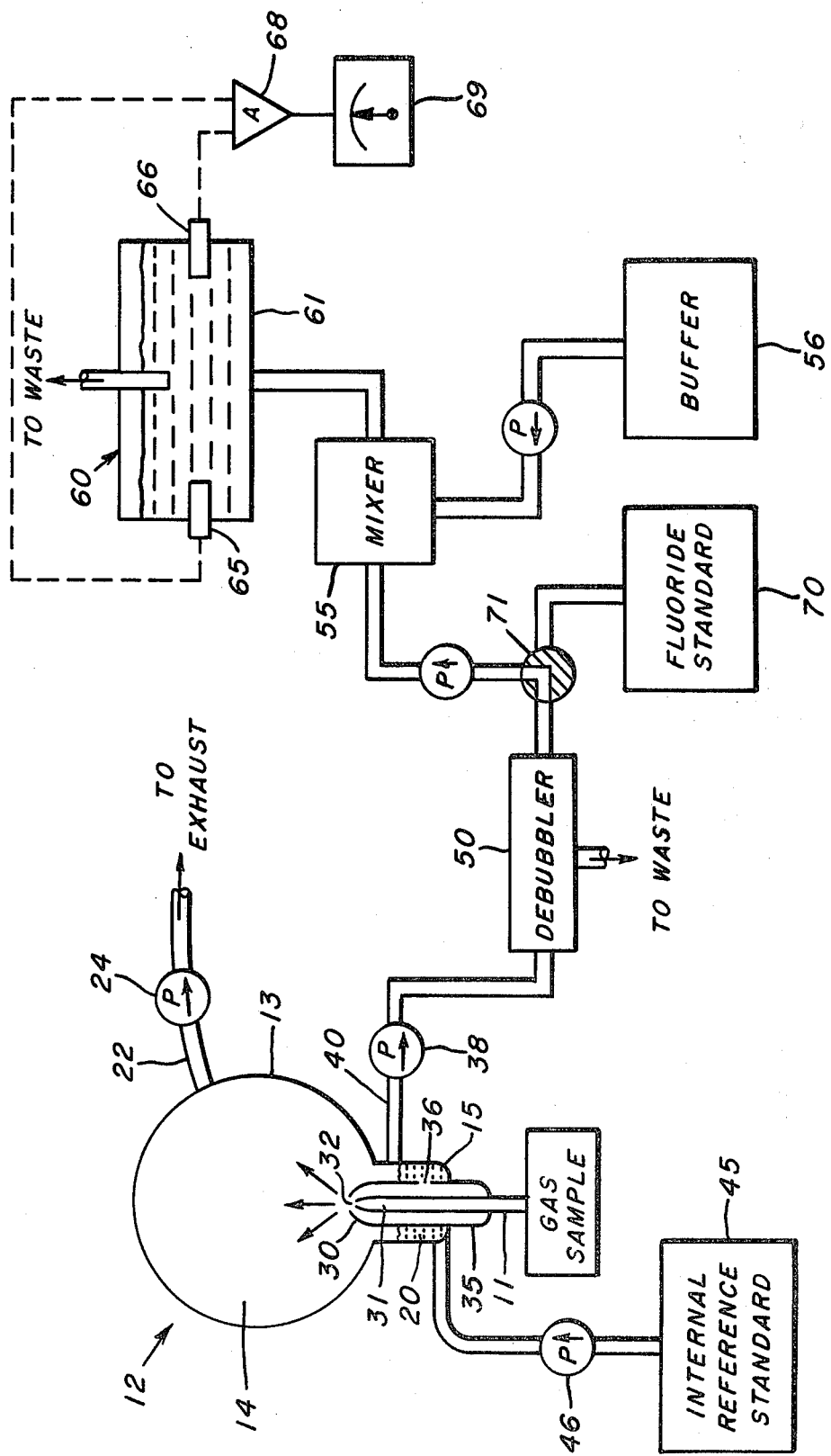

MEASUREMENT OF GASEOUS FLUORIDE CONCENTRATION USING AN INTERNAL REFERENCE SOLUTION

BACKGROUND OF THE INVENTION

The present invention relates to methods for determining the concentration of fluoride in gases. In an industrial setting, such gases result from electrolytic processes for production of aluminum by electrolysis of alumina in a molten cryolite bath.

Processes for measuring gaseous fluoride concentrations are known in the prior art. However, each of these prior art processes suffers from one or more serious disadvantages making it less than completely suitable for its intended purpose.

For example, one prior art process in commercial use prior to the present invention relied upon mixing a sample of fluoride-containing gas with water in a gas scrubber to form a fluoride-containing solution. A known concentration of bromide ion was then added to the solution, and the concentration of fluoride ion was measured in a potentiometric apparatus.

In this prior art process, error was introduced by evaporation of water in the scrubber. An attempt to compensate for this error resulted in the introduction of error caused by loss of mist from the scrubber. This prior art process was also sensitive to variations in the flow rate of water to the scrubber.

It is a principal objective of the invention to provide a method for determining fluoride concentration in a fluoride-containing gas, wherein the method eliminates errors caused by evaporation of water from the gas scrubber and of water supplied to the gas scrubber.

It is a related objective of the invention to provide a method for determining fluoride concentrations in a gas that avoids introduction of other errors.

Additional objects and advantages of the present invention will become apparent to persons skilled in the art from the following specification, taken in conjunction with the drawing.

SUMMARY OF THE INVENTION

In accordance with the present invention, a sample of a fluoride-containing gas is mixed in a gas scrubber with an aqueous internal reference solution containing a known concentration of chloride, bromide or iodide ion. Mixture of the gas with the reference solution in the scrubber produces a fluoride-containing solution that is collected and transmitted to a potentiometric apparatus.

The potentiometric apparatus includes a first electrode and a second electrode, both contacting the fluoride-containing solution. The first electrode has an element sensitive to the fluoride ion concentration, and the second electrode has an element sensitive to chloride, bromide or iodide ion concentration. The fluoride-containing solution is buffered to maintain its pH below 8 in the potentiometric apparatus.

In a preferred embodiment, the internal reference solution comprises dissolved potassium bromide, and the second electrode has an element sensitive to concentration of bromide ion.

BRIEF DESCRIPTION OF THE DRAWING

The sole FIGURE is a flow sheet diagram, schematically illustrating the method of the invention.

DETAILED DESCRIPTION OF A PREFERRED EMBODIMENT

In accordance with the present invention, a sample of fluoride-containing gas is scrubbed with an aqueous solution in a gas scrubber to form a fluoride-containing solution that is collected and transmitted to a potentiometric apparatus. This apparatus measures fluoride concentration in the fluoride-containing solution, and fluoride concentration in the gas is calculated based upon the flow rate of aqueous solution to the gas scrubber.

Referring now to the drawing, the invention is practiced by leading a sample of a fluoride-containing effluent stack gas through a sampling line 11 into a gas scrubber 12. The sampling line 11 is preferably made from polytetrafluoroethylene or a similar fluoride-resistant material. The stack gas is transmitted without filtration into the scrubber 12.

The preferred gas scrubber 12 includes a bulb 13 defining a large, generally spherical chamber 14. In a lower portion of the scrubber 12, a reservoir 15 holds an internal reference standard or internal reference solution 20 containing dissolved potassium bromide and fluoride ion dissolved from the stack gas. Scrubbed gas is removed from the chamber 14 through a side arm 22 by means of a diaphragm vacuum pump 24 that is rated for continuous operation. The side arm 22 also acts as a moisture trap to prevent excessive losses of moisture from the chamber 14.

The scrubber 12 includes an aspirator 30 that continuously projects a spray of gas and reference solution into the chamber 14. The aspirator 30 includes a gas supply tube 31 having an inlet orifice 32 communicating with the chamber 14, and a liquid supply tube 35 having an uptake opening 36 in the reservoir 15. The aspirator 30 causes a high velocity spray of the gas and reference solution to enter the chamber 14, where the fluoride ion is dissolved from the gas. A fluoride-containing solution collects on the inside wall of the bulb 13 where it flows downwardly to the reservoir 15. The scrubber 12 routinely achieves an efficiency of about 95 to 97% in removing fluoride from the stack gas. A constant liquid level is maintained in the reservoir 15 by continuously removing the fluoride-containing solution with a positive displacement pump 38 through a liquid outlet line 40.

In the improved method of the present invention, the reference solution contains a known concentration of chloride, bromide or iodide ion. The reference solution is made up by adding a known quantity of a water-soluble chloride, bromide or iodide salt to a known volume of water, thereby to form an aqueous solution. Solutions of potassium bromide and sodium bromide are preferred. A particularly preferred reference solution contains precisely 100.0 mg/l of dissolved KBr. The reference solution is stored in a supply tank 45 and fed to the reservoir 15 in a continuous flow at a costant rate by a pump 46.

Gas flow rate remains constant because of the small size of the limiting orifice 32. The gas flow rate is readily adjusted by changing the size of the orifice 32. This change is easily accomplished because a standard tapered joint is used as a connection at a lower portion of the reservoir 15. Additional details of the gas scrubber 12 are provided in U.S. Pat. No. 3,960,523, the disclosure of which is incorporated by reference to the extent not inconsistent with the present invention.

Samples of fluoride-containing solution are transmitted to a debubbler 50 where bubbles are removed. The samples are next pumped to a mixer 55 where an alkaline total ionic strength adjustment buffer is added from a bottle 56. The pH of the solution is typically about 2 to 3 prior to addition of buffer and about 4 to 5 after addition of buffer. It is important to maintain pH of the solution below 8 at this point in order to minimize interference by hydroxide ion with determination of the fluoride ion concentration in the potentiometric apparatus 60.

Buffered samples of the solution are delivered to a potentiometric apparatus 60 having a thermostatically controlled solution container 61. The apparatus 60 includes a first electrode 65 contacting solution held in the container 61 and a second electrode 66 also contacting the solution. A preferred first electrode 65 has a crystalline fluoride first element comprising 99.5% lanthanum trifluoride and 0.5% europium trifluoride. The first element is sensitive to concentration of fluoride ion in the solution. The preferred first electrode 65 is disclosed in Frant U.S. Pat. No. 3,431,182, which patent is incorporated herein by reference to the extent not inconsistent with the present invention.

The second electrode 66 has a second element that is sensitive to the concentration of chloride, bromide or iodide ion in the solution. A particularly preferred second element comprises a mixture of silver sulfide and silver bromide. The preferred second electrode 66 is disclosed in Ross et al. U.S. Pat. No. 3,563,874, which patent is incorporated herein by reference to the extent not inconsistent with the present invention.

Samples of the fluoride-containing solution flow past the surfaces of the two electrodes 65, 66 at a controlled rate, and their electric potential is measured. An operational differential amplifier 68 amplifies the potential difference signal received from the electrodes 65, 66, and the amplified signal is displayed on a meter and recorder 69.

The apparatus 60 is calibrated with a fluoride standard solution comprising a known concentration of fluoride ion and 100 mg/l potassium bromide dissolved in water. The fluoride standard is supplied from a bottle 70 connected to a three-way valve 71. The valve 71 is normally open from the debubbler 50 to the potentiometric apparatus 60 and closed between the standard bottle 70 and potentiometric apparatus 60. However, when calibrating the apparatus 60, the valve 71 is open from the standard bottle 70 to the apparatus 60 and closed between the debubbler 50 and apparatus 60. The apparatus 60 may be calibrated automatically at periodic intervals if desired.

The gas scrubber 12 collects fluorides from a known volume of fluoride-containing solution. The volume of gas is known because the limiting orifice 32 and vacuum pump 24 maintain gas flow rate at a known, fixed value. The volume of solution is known because the pumps 46, 38 maintain solution flow rate at a known, fixed value. Accordingly, the concentration of fluoride in the gas is calculated using the following equation:

$$A = \frac{B \times C}{D} \quad (1)$$

wherein
A = concentration of fluoride in the gas, in micrograms per m$^3$,
B = solution flow rate, ml/min;
C = measured concentration of fluoride in the solution, in micrograms per ml; and
D = gas flow rate, in m$^3$/min.

In the prior art, the gas was scrubbed with water in the gas scrubber 12 and a potassium bromide reference solution was added along with the buffer solution, just before the fluoride-containing solution entered the potentiometric apparatus 60. Careful scrutiny of the situation has recently revealed that equation (1) is actually only partially descriptive of the true workings of the gas scrubber 12.

The major problem in the prior art appears to be failure to adequately account for the mass balance of water used to scrub fluoride from the gas. It is essential that a known volume of collection liquid be used in equation (1) or the results calculated will be in error. An accurate volume flow rate of the scrubbing solution into the scrubber bulb is known and for the purpose of explanation will be defined here as $V_{in}$. Once this volume of water is pumped into the chamber 14, three things will happen:

1. The majority of the water is nebulized and impinged on the inside of the bulb. This water then flows back to reservoir 15 and is pumped out of the scrubber 12. This volume will be identified as $V_{out}$.

2. Part of the aspirated water creates droplets that are small enough to be entrained in the gas flow and carried out of the scrubber 12. These small droplets of water have some of the dissolved fluoride in them. This volume of entrained mist will be defined as $V_{mist}$.

3. Part of the volume pumped into the chamber 14 will evaporate. Evaporation rate will be a function of the temperature, pressure, and relative humidity of the incoming gas. This volume will be defined as $V_{evap}$. The following water mass balance equation can now be written:

$$V_{in} = V_{out} + V_{mist} + V_{evap} \quad (2)$$

It therefore follows that if a certain mass of HF or other fluoride (defined as gF$^-$) in a certain mass of gas (D) is scrubbed by the scrubber, the fluoride will dissolve in the liquid water and not the gaseous water. The following equation can then be used to define C in equation (1):

$$C = \frac{gF^-}{V_{out} + V_{mist}} \quad (3)$$

Keeping in mind that the true concentration of fluoride in the gas is gF$^-$/D and substituting equations (2) and (3) into equation (1), the following equation results:

$$A = \frac{\frac{gF^-}{(V_{out} + V_{mist})} \times (V_{out} + V_{mist} + V_{evap})}{D} \quad (4)$$

$$A = \frac{\frac{gF^-}{V_{in} - V_{evap}} \times V_{in}}{D}$$

In other words, the concentration will read high by a ratio of $V_{in}/(V_{in} - V_{evap})$.

An equation that was used prior to the present invention represented an attempt to correct the results for evaporation losses. This equation used a so-called evaporation correction factor. The correction factor really removed both evaporation and mist from the calculation. Use of the evaporation correction factor involved using $V_{out}$ for B in equation (1), which would then read as follows:

$$A = \frac{\frac{gF^-}{V_{out} + V_{mist}} \times (V_{out})}{D} \quad (5)$$

and the results would be low by the ratio of $V_{out}/(V_{out}+V_{mist})$. In summary, equation (4) stated that the results would be high unless evaporation was negligible while equation (5) states the results would be low unless mist loss was negligible.

The above errors are dynamically corrected by the method of the present invention. The following discussion explains the theory of dynamically correcting errors.

Response of the fluoride-sensitive electrode is known to obey the following equation:

$$E_F = E_F° - m_F \log (F^-) \quad (6)$$

where
E is a potential in volts measured by the fluoride-sensitive electrode;
$E_F°$ is a constant;
$m_F$ is a constant; and
$(F^-)$ is the fluoride ion concentration in mass of fluoride per volume (i.e., micrograms fluoride per ml).

The reference electrode is a bromide-sensitive electrode that obeys the following response equation:

$$E_{Br} = E_{Br}° - m_{Br} \log (Br^-) \quad (7)$$

where the above symbols have definitions analogous to those of the fluoride-sensitive electrode but involve bromide instead of fluoride.

The actual measurement made by the potentiometric apparatus is the potential difference between the two electrodes and can be expressed as the difference between equations (6) and (7).

$$E_{Br} = E_{Br}° - m_{Br}\log (Br^-) - [E_F = E_F° - m_F\log (F)^-]$$

$$\Delta E = \Delta E° + \Delta m \log (F^-)/(Br^-) \quad (8)(a)$$

Because the fluoride concentration $(F^-)$ and bromide concentration $(Br^-)$ are both in units of mass per unit volume, the volume term will cancel and the equation will read:

$$\Delta E = \Delta E° + \Delta m \log (gF^-/gBr^-) \quad (8)(b)$$

which indicates the measurement will actually be a measure of the weight ratio of fluoride to bromide. The present invention takes advantage of this by adding the reference bromide ion to the standards and the water instead of to the buffer solutions. Since the reference bromide ion is in the water and standards, any volume changes that occur in the scrubber affect the bromide ion and fluoride ion equally. The solutions with the internal reference standard are calibrated to a standard volume $V_{in}$. Therefore, even though evaporation and mist losses will occur, the fluoride concentration is behaving as though it were still dissolved in a solution having a volume of $V_{in}$. This will cause equation (4) to behave as follows:

$$A = \frac{\frac{gF^-}{V_{effective}} \times V_{in}}{D}$$

where
$V_{effective}$ = the volume that the fluoride to bromide ratio is referenced to = $V_{in}$.
Therefore, $A = gF^-/D$ which is now possible due to the use of the internal reference standard in accordance with the method of the present invention.

While the foregoing detailed description of my invention has been made with reference to a particularly preferred embodiment thereof, persons skilled in the art will understand that numerous changes and modifications can be made without materially departing from the spirit and scope of the following claims.

What is claimed is:
1. In a method for determining fluoride concentration in a fluoride-containing gas, said method including the steps of
(a) mixing a sample of the gas with water in a gas scrubber, thereby dissolving fluoride ion and forming a fluoride-containing solution,
(b) collecting said fluoride-containing solution,
(c) determining the concentration of fluoride ion in said fluoride-containing solution in a potentiometric apparatus by measuring the electric potential developed between a first electrode contacting said fluoride-containing solution and a second electrode contacting said fluoride-containing solution, said first electrode having an element sensitive to the fluoride ion concentration and insensitive to chloride ion concentration, and said second electrode having an element sensitive to the concentration of an ion selected from the group consisting of chloride, bromide and iodide ions,
the improvement wherein, for the purpose of reducing error caused by evaporation of water and without introducing error resulting from loss of mist from the gas scrubber, said method further comprises the steps of
(d) dissolving a known quantity of a water-soluble chloride, bromide or iodide salt in a known volume of water, thereby to form an aqueous internal reference solution,
(e) mixing said sample of the gas with the internal reference solution of step (d) in step (a), and
(f) maintaining the pH of said fluoride-containing solution below 8 during step (c).
2. The method of claim 1 wherein the ion in said aqueous internal reference solution is bromide ion, and said second electrode has an element sensitive to the bromide ion concentration.
3. The method of claim 2 wherein said water-soluble chloride, bromide or iodide salt is potassium bromide or sodium bromide.
4. The method of claim 1 wherein the gas and the internal reference solution each flow to the scrubber continuously in step (a), and said improvement corrects for error caused by changes in the flow rate of said internal reference solution and by evaporation of water from said internal reference solution.
5. The method of claim 1 wherein the gas and the internal reference solution each flow to the scrubber continuously in step (a), and said improvement prevents the determination of fluoride ion concentration in step (c) from reading too high by a factor of $$\frac{V_{in}}{V_{in} - V_{evap}}$$

wherein $V_{in}$ is the volume flow rate of reference solution to the scrubber and $V_{evap}$ is the volume rate of evaporation of water from the scrubber.

6. A method for continuously determining fluoride concentration in a fluoride-containing gas, said method comprising
   (a) dissolving a known quantity of a water-soluble bromide in a known volume of water, thereby to form an aqueous internal reference solution,
   (b) continuously mixing a sample of the fluoride-containing gas with the internal reference solution in a gas scrubber, thereby dissolving fluoride ion and forming a fluoride-containing solution,
   (c) continuously collecting said fluoride-containing solution,
   (d) continuously determining the concentration of fluoride ion in said fluoride-containing solution in a potentiometric apparatus by measuring the electric potential developed between a first electrode contacting said fluoride-containing solution and a second electrode contacting said fluoride-containing solution, said first electrode having a lanthanum trifluoride-europium trifluoride element sensitive to the fluoride ion concentration and insensitive to chloride ion concentration, and said second electrode having a silver sulfide-silver bromide element sensitive to the bromide ion concentration, and
   (e) adding a buffer to said fluoride-containing solution, the quantity of said buffer being sufficient to maintain pH of said fluoride-containing solution below 8 in step (d).

7. The method of claim 1 wherein said fluoride-containing gas is an effluent stack gas resulting from an electrolytic process carried out in a molten cryolite bath.

8. The method of claim 1 wherein the pH of said fluoride-containing solution is maintained at about 4 to 5 in step (c).

9. The method of claim 3 wherein said internal reference solution contains precisely 100.0 mg/l of dissolved KBr.

10. The method of claim 6 wherein said fluoride-containing gas is an effluent stack gas resulting from an electrolytic process carried out in a molten cryolite bath.

11. The method of claim 6 wherein the quantity of said buffer is sufficient to maintain pH of said fluoride-containing solution at about 4 to 5 in step (d).

* * * * *